(12) United States Patent
Jiang et al.

(10) Patent No.: US 7,629,443 B2
(45) Date of Patent: Dec. 8, 2009

(54) NEUTRALIZING MONOCLONAL ANTIBODIES AGAINST SEVERE ACUTE RESPIRATORY SYNDROME-ASSOCIATED CORONAVIRUS

(75) Inventors: Shibo Jiang, Fresh Meadows, NY (US); Yuxian He, Bronx, NY (US)

(73) Assignee: New York Blood Center, Inc., New York, NY (US)

( * ) Notice: Subject to any disclaimer, the term of this patent is extended or adjusted under 35 U.S.C. 154(b) by 618 days.

(21) Appl. No.: 11/351,108

(22) Filed: Feb. 8, 2006

(65) Prior Publication Data

US 2006/0240551 A1 Oct. 26, 2006

Related U.S. Application Data

(63) Continuation-in-part of application No. 11/141,925, filed on May 31, 2005, now abandoned.

(60) Provisional application No. 60/651,046, filed on Feb. 8, 2005, provisional application No. 60/576,118, filed on Jun. 2, 2004.

(51) Int. Cl.
*C12P 21/08* (2006.01)
(52) U.S. Cl. .................................. 530/388.3
(58) Field of Classification Search ........................ None
See application file for complete search history.

(56) References Cited

U.S. PATENT DOCUMENTS

2005/0249739 A1* 11/2005 Marasco et al. .......... 424/159.1

OTHER PUBLICATIONS

Sui et al (PNAS 101:2536-2541, 2004).*
May 3, 2007 PCT Invitation to Pay Additional Fees and, Where Applicable, Protest Fees, for New York Blood Center, International Application No. PCT/US06/04599, filed Feb. 8, 2006.
Jun. 4, 2007 Response to PCT Invitation to Pay Additional Fees and, Where Applicable, Protest Fees, for New York Blood Center, International Application No. PCT/US06/04599, filed Feb. 8, 2006.
Jan. 31, 2008 PCT International Search Report and Written Opinion, for New York Blood Center, International Application No. PCT/US06/04599, filed Feb. 8, 2006.
Choy et al. "Synthetic peptide studies on the severe acute respiratory syndrome (SARS) coronavirus spike glycoprotein: perspective for SARS vaccine development." Clinical Chemistry 2004, 50(6), 1036-1042.
Drosten, C. et al., 2003, "Identification of a Novel Coronavirus in Patients with Severe Acute Respiratory Syndrome", N. Engl. J. Med. 348:1967-1976.
Ksiazek, T.G. et al., 2003, "A Novel Coronavirus Associated with Severe Acute Respiratory Syndrome", N. Engl. J. Med. 348:1953-1966.
Peiris, J.S. et al., 2003, "Coronavirus as a possible cause of severe acute respiratory syndrome", Lancet 361:1319-1325.
Marra, M.A. et al., 2003, "The Genome Sequence of the SARS-Associated Coronavirus", Science 300:1399-1404.
Rota, P.A. et al., 2003, "Characterization of a Novel Coronavirus Associated with Severe Acute Respiratory Syndrome", Science 300:1394-1399.
Du, L. et al., 2007, "Cleavage of spike protein of SARS coronavirus by protease factor Xa is associated with viral infectivity", Biochem. Biophys. Res. Commun. 359:174-179.
Marshall, E. et al., 2004, "Caution Urged on SARS vaccines", Science 303:944-946.
Peiris, J.S. et al., 2004, "Severe acute respiratory syndrome", Nat. Med. 10:S88-S97.
Du, L. et al., 2007, "Receptor-binding domain of SARS-CoV spike protein induces long-term protective immunity in an animal model", Vaccine 25:2832-2838.
Holmes, K.V. et al., 2003, "Virology: The SARS Coronavirus: A postgenomic Era", Science 300:1377-1378.
Holmes, K.V., 2003, "SARS coronavirus: a new challenge for prevention and therapy", J. Clin. Invest. 111:1605-1609.
He, Y. et al., 2006, "Cross-Neutralization of Human and Palm Civet Severe Acute Respiratory Syndrome Coronavirus by Targeting the Receptor-Binding Domain of Spike Protein", J. Immunol. 176, 6085-6092.
He, Y. et al., 2006, "Antigenic and Immunogenic Characterization of Recombinant Baculovirus-Expressed Severe Acute Respiratory Syndrome Coronavirus Spike Protein: Implication for Vaccine Design", J. Virol. 80:5757-5767.
Chen, Z. et al., 2005, "Recombinant Modified Vaccinia Virus Ankara Expressing the Spike Glycoprotein of Severe Acute Respiratory Syndrome Coronavirus Induces Protective Neutralizing Antibodies Primarily Targeting the Receptor Binding Region", J. Virol. 79:2678-2688.
Bosch, B.J. et al., 2004, "Severe acute respiratory syndrome coronavirus (SARS-CoV) infection inhibition using spike protein heptad repeat-derived peptides", Proc. Natl. Acad. Sci. USA 101:8455-8460.
Ingallinella, P., E. et al., 2004, "Structural characterization of the fusion-active complex of severe acute respiratory syndrome (SARS) coronavirus", Proc. Natl. Acad. Sci. USA 101:8709-8714.

(Continued)

*Primary Examiner*—Mary E Mosher
(74) *Attorney, Agent, or Firm*—Louis C. Cullman; K&L Gates LLP

(57) ABSTRACT

The present invention provides an isolated antibody capable of binding to the receptor-binding domain of the spike protein of the severe acute respiratory syndrome-associated coronavirus (SARS-CoV) so as to competitively inhibit the binding of the SARS-CoV to host cells. These mAbs or substances can be used: 1) as passive-immunizing agents for prevention of SARS-CoV infection; 2) as biological reagents for diagnosis of SARS-CoV infection; 3) as immunotherapeutics for early treatment of SARS-CoV infection; and 4) as probes for studying the immunogenicity, antigenicity, structure, and function of the SARS-CoV S protein.

1 Claim, 3 Drawing Sheets

OTHER PUBLICATIONS

Liu, S. et al., 2004, "Interaction between the heptad repeat 1 and 2 regions in spike protein of SARS-associated coronavirus: implication for virus fusogenic mechanism and identification of fusion inhibitors", Lancet 363:938-947.

Yi, C. E. et al., 2005, "Single Amino Acid Substitutions in the Severe Acute Respiratory Syndrome Coronavirus Spike Glycoprotein Determine Viral Entry and Immunogenicity of a Major Neutralizing Domain", J. Virol. 79:11638-11646.

Du, L. et al., 2006, "Recombinant adeno-associated virus expressing the receptor-binding domain of severe acute respiratory syndrome coronavirus S protein elicits neutralizing antibodies: Implication for developing SARS vaccines", Virology 353:6-16.

Bosch, B.J. et al., 2003, "The Coronavirus Spike Protein Is a Class I Virus Fusion Protein: Structural and Functional Characterization of the Fusion Core Complex", J. Virol. 77:8801-8811.

Xu, Y. et al., 2004, "Crystal Structure of Severe Acute Respiratory Syndrome Coronavirus Spike Protein Fusion Core", J. Biol. Chem. 279:49414-49419.

Li, W. et al., 2003, "Angiotensin-converting enzyme 2 is a functional receptor for the SARS coronavirus", Nature 426:450-454.

Dimitrov, D.S., 2003, "The Secret Life of ACE2 as a receptor for the SARS Virus", Cell 115:652-653.

Prabakaran, P. et al., 2004, "A model of the ACE2 structure and function as a SARS-CoV receptor", Biochem. Biophys. Res. Commun. 314:235-241.

Wang, P. et al., 2004, "Expression cloning of functional receptor used by SARS coronavirus", Biochem. Biophys. Res. Commun. 315:439-444.

Xiao, X., S. Chakraborti et al., 2003, "The SARS-CoV S glycoprotein: expression and functional characterization", Biochem. Biophys. Res. Commun. 312:1159-1164.

Wong, S.K. et al., 2004, "A 193-Amino-Acid Fragment of the SARS Coronavirus S Protein Efficiently Binds Angiotensin-converting Enzyme 2", J. Biol. Chem. 279:3197-3201.

Babcock, G.J. et al., 2004, "Amino Acids 270 to 510 of the Severe Acute Respiratory Syndrome Coronavirus Spike Protein Are Required for Interaction with Receptor", J. Virol. 78:4552-4560.

He, L. et al., 2006, "Expression of elevated levels of pro-inflammatory cytokines in SARS-CoV-infected ACE2+ cells in SARS patients: relation to the acute lung injury and pathogenesis of SARS", J. Pathol. 210:288-297.

Liu, L. et al., 2007, "Natural Mutations in the Receptor Binding Domain of Spike Glycoprotein Determine the Reactivity of Cross-Neutralization between Palm Civet Coronavirus and Severe Acute Respiratory Syndrome Coronavirus", J Virol. 81:4694-700.

Buchholz, U.J. et al., 2004, "Contributions of the structural proteins of severe acute respiratory syndrome coronavirus to protective immunity", Proc. Natl. Acad. Sci. USA 101:9804-9809.

Yang, Z.Y. et al., 2004, "A DNA vaccine induces SARS coronavirus neutralization and protective immunity in mice", Nature 428:561-564.

Bisht, H. et al., 2004, "Severe acute respiratory syndrome coronavirus spike protein expressed by attenuated vaccinia virus protectively immunizes mice", Proc. Natl. Acad. Sci. USA 101:6641-6646.

Bukreyev, A. et al., 2004, "Mucosal immunisation of African green monkeys (*Cercopithecus aethiops*) with an attenuated parainfluenza virus expressing the SARS coronavirus spike protein for the prevention of SARS", Lancet 363:2122-2127.

He, Y. et al., "Receptor-binding domain of SARS-CoV spike protein induces highly potent neutralizing antibodies: implication for developing subunit vaccine", Biochem. Biophys. Res. Commun. 324:773-781, (2004).

He, Y. et al., 2004, "Inactivated SARS-CoV vaccine elicits high titers of spike protein-specific antibodies that block receptor binding and virus entry", Biochem. Biophys. Res. Commun. 325:445-452.

Morrison, S.L. et al., 1984, "Chimeric human antibody molecules: mouse antigen-binding domains with human constant region domains", Proc. Natl. Acad. Sci. USA 81:6851-6855.

He, Y. et al., 2005, "Receptor-Binding Domain of Severe Acute Respiratory Syndrome Coronavirus Spike Protein Contains Multiple Conformation-Dependant Epitopes that Induce Highly Potent Neutralizing Antibodies", J. Immunol. 174:4908-4915.

He, Y. et al., 2005, "Identification of Immunodominant Epitopes on the Membrane Protein of the Severe Acute Respiratory Syndrome-Associated Coronavirus", J. Clin. Microbiol. 43:3718-26.

He, Y. et al., 2006, "A single amino acid substitution (R441A) in the receptor-binding domain of SARS coronavirus spike protein disrupts the antigenic structure and binding activity", Biochem. Biophys. Res. Commun. 344:106-113.

He, Y. et al., 2006, "Identification and characterization of novel neutralizing epitopes in the receptor-binding domain of SARS-CoV spike protein; Revealing the critical antigenic determinants in inactivated SARS-CoV vaccine", Vaccine. 24:5498-5508.

Zhang, H., G. Wang et al., 2004, "Identification of an Antigenic Determinant on the S2 Domain of the Severe Acute Respiratory Syndrome Coronavirus Spike Glycoprotein Capable of Inducing Neutralizing Antibodies", J. Virol. 78:6938-6945.

Nie, Y. et al., 2004, "Neutralizing Antibodies in Patients with Severe Acute Respiratory Syndrome-Associated Coronavirus Infection", J. Infect. Dis. 190:1119-1126.

Hofmann, H., K. Hattermann et al., 2004, "S Protein of Severe Acute Respiratory Syndrome-Associated Coronavirus Mediates Entry into Hepatoma Cell Lines and Is Targeted by Neutralizing Antibodies in Infected Patients", J. Virol. 78:6134-6142.

Lu, L. et al., 2004, "Immunological Characterization of the Spike Protein of the Severe Acute Respiratory Syndrome Coronavirus", J. Clin. Microbiol. 42:1570-1576.

He, Y. et al., 2004, "Identification of Immunodominant Sites on the Spike Protein of Severe Acute Respiratory Syndrome (SARS) Coronavirus: Implication for Developing SARS Diagnostics and Vaccines", J. Immunol. 173:4050-4057.

Wilson, J.A. et al., 2000, "Epitopes Involved in Antibody-Mediated Protection from Ebola virus", Science 287:1664-1666.

He, Y. et al., 2005, "Identification of a critical neutralization determinant of severe acute respiratory syndrome (SARS)-associated coronavirus: Importance for designing SARS vaccines", Virology 334:74-82.

Sui, J. et al., 2004, "Potent neutralization of severe acute respiratory syndrome (SARS) coronavirus by a human mAb to S1 protein that blocks receptor association", Proc. Natl. Acad. Sci. USA 101:2536-2541.

Subbarao, K., J. McAuliffe et al., 2004, "Prior infection and Passive Transfer of Neutralizing Antibody Prevent Replication of Severe Acute Respiratory Syndrome Coronavirus in the Respiratory Tract of Mice", J. Virol. 78:3572-3577.

ter Meulen, J. et al., 2004, "Human monoclonal antibody as prophylaxis for SARS coronavirus infection in ferrets", Lancet 363:2139-2141.

Traggiai, E., S. Becker et al., 2004, "An efficient method to make human monoclonal antibodies from memory B cells: potent neutralization of SARS coronavirus", Nat. Med. 10:871-875.

Jiang, S. et al., 2005, "SARS vaccine development", Emerg. Infect. Dis. 11:1016-1020.

Ding, Y. et al., 2004, "Organ distribution of severe acute respiratory syndrome (SARS) associated coronavirus (SARS-CoV) in SARS patients: implication for pathogenesis and virus transmission pathways", J. Pathol. 203:622-630.

Breedveld, F.C., 2000, "Therapeutic monoclonal antibodies", Lancet 355:735-740.

Xu, Z., et al., 2002, "The in vitro and in vivo protective activity of monoclonal antibodies directed against Hantaan virus: potential application for immunotherapy and passive immunization", Biochem. Biophys. Res. Commun. 298:552-558.

van den Brink, E. N. et al., 2005, "Molecular and Biological Characterization of Human Monoclonal Antibodies Binding to the Spike and Nucleocapsid Proteins of Severe Acute Respiratory Syndrome Coronavirus", Journal of Virology 79:1635-1644.

* cited by examiner

Fig. 1

Fig. 3
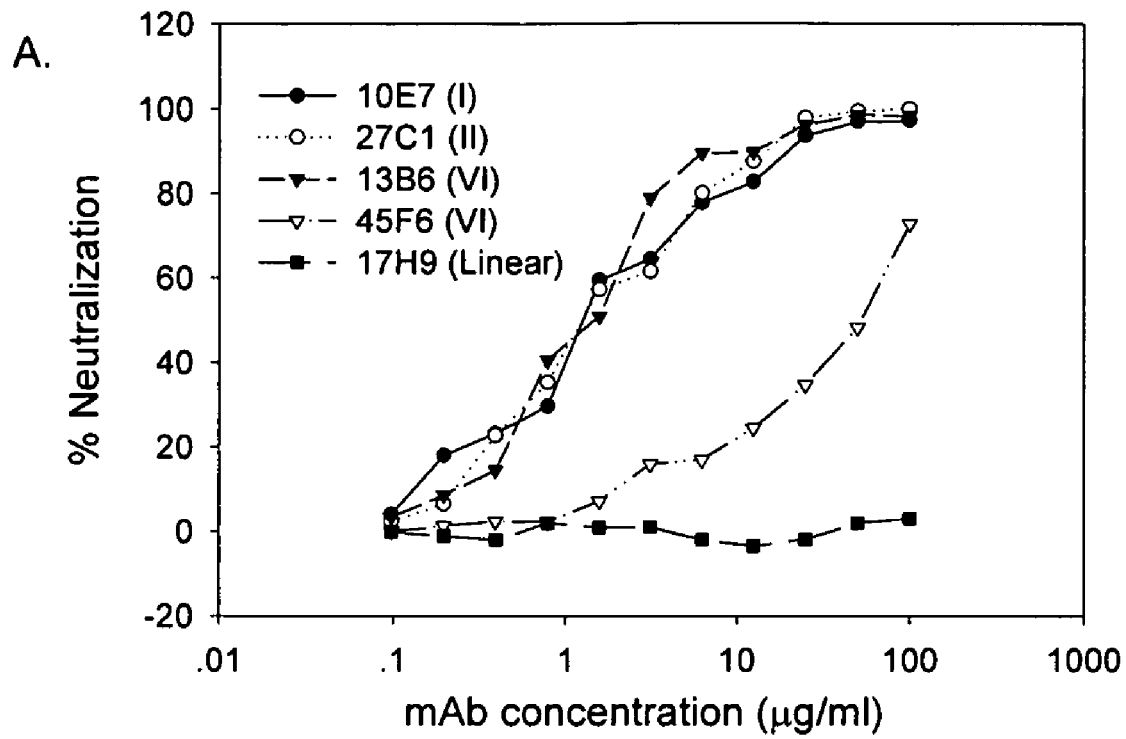
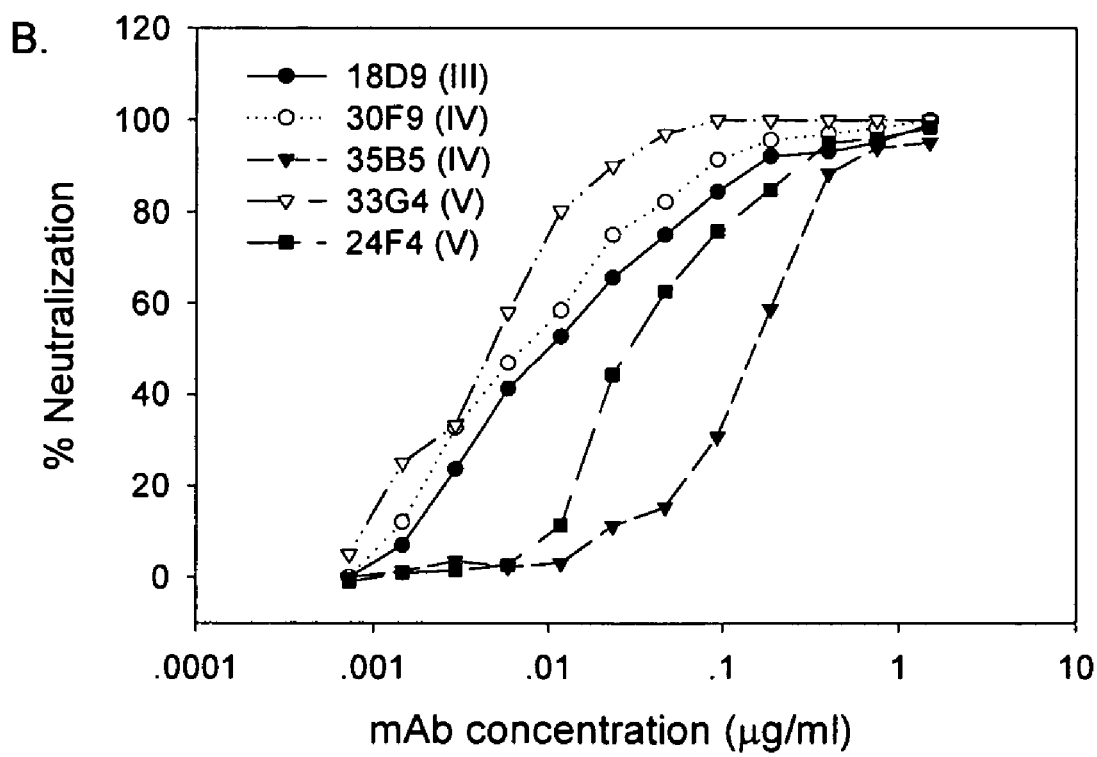

SEQUENCE LISTING

```
<160> NUMBER OF SEQ ID NOS: 4

<210> SEQ ID NO 1
<211> LENGTH: 17
<212> TYPE: PRT
<213> ORGANISM: Human coronavirus

<400> SEQUENCE: 1

Asn Tyr Asn Tyr Lys Tyr Arg Tyr Leu Arg His Gly Lys Leu Arg Pro
1               5                   10                  15

Phe

<210> SEQ ID NO 2
<211> LENGTH: 17
<212> TYPE: PRT
<213> ORGANISM: Human coronavirus

<400> SEQUENCE: 2

Tyr Leu Arg His Gly Lys Leu Arg Pro Phe Glu Arg Asp Ile Ser Asn
1               5                   10                  15

Val

<210> SEQ ID NO 3
<211> LENGTH: 17
<212> TYPE: PRT
<213> ORGANISM: Human coronavirus

<400> SEQUENCE: 3

Arg Pro Phe Glu Arg Asp Ile Ser Asn Val Pro Phe Ser Pro Asp Gly
1               5                   10                  15

Lys

<210> SEQ ID NO 4
<211> LENGTH: 10
<212> TYPE: PRT
<213> ORGANISM: Human coronavirus

<400> SEQUENCE: 4

Arg Pro Phe Glu Arg Asp Ile Ser Asn Val
1               5                   10
```

NEUTRALIZING MONOCLONAL ANTIBODIES AGAINST SEVERE ACUTE RESPIRATORY SYNDROME-ASSOCIATED CORONAVIRUS

CROSS-REFERENCE TO RELATED APPLICATIONS

The present application claims the benefit of U.S. Ser. No. 60/651,046, filed Feb. 8, 2005, and is a continuation-in-part of U.S. Ser. No. 11/141,925, filed May 31, 2005, now abandoned which claims the benefit of U.S. Ser. No. 60/576,118, filed Jun. 2, 2004. References are made to various publications throughout this application. Accordingly, such references and their corresponding disclosures are hereby incorporated by reference in their entireties into this application to provide a more thorough description of the state of the art to which this invention pertains.

BACKGROUND OF THE INVENTION

Severe acute respiratory syndrome (SARS) is a recently-recognized, febrile severe lower respiratory illness that is the result of an infection caused by a novel coronavirus (SARS-CoV) (1-5). The global outbreak of SARS was contained, but concerns remain over the possibility of future recurrences, especially with recent reports of laboratory-acquired infections (6). However, no effective treatment or prophylaxis is currently available to combat this deadly virus (7, 8).

Like other coronaviruses, SARS-CoV is an enveloped virus containing a large, positive-stranded RNA genome that encodes viral replicase proteins and structural proteins including spike (S), membrane (M), envelope (E), nucleocapsid (N), and several uncharacterized proteins (4, 5, 9). Phylogenetic analyses indicate that SARS-CoV is distinct from the three known antigenic groups of coronaviruses. Therefore, post-genomic characterization of SARS-CoV is important for developing anti-SARS therapeutics and vaccines (10, 11).

Coronavirus infection is initiated by attachment of the S protein to the specific host receptor, which triggers a conformational change in the S protein. The S protein of SARS-CoV is a type I transmembrane glycoprotein with a predicted length of 1,255 amino acids that contains a leader (residues 1-14), an ectodomain (residues 15-1190), a transmembrane domain (residues 1191-1227), and a short intracellular tail (residues 1227-1255) (5). Unlike many other coronaviruses, such as the mouse hepatitis virus (MHV)(12, 13), in which the S protein is post-translationally cleaved into S1 and S2 subunits, no typical cleavage motif has been identified in the SARS-CoV S protein (5). Nonetheless, its S1 and S2 domains were predicted by sequence alignment with other coronavirus S proteins (5, 14). The S2 domain (residues 681-1255) of SARS-CoV S protein containing a putative fusion peptide and two heptad repeat (HR1 and HR2) regions is responsible for fusion between viral and target cell membranes. It has been found that the HR1 and HR2 regions can associate to form a six-helix bundle structure (15-18), resembling the fusion-active core of the HIV gp41 (19) and the MHV S protein (20, 21). The S1 domain of SARS-CoV S protein mediates virus-binding with angiotensin-converting enzyme 2 (ACE2), the functional receptor for SARS-CoV on susceptible cells (22-25). Recently, a 193-amino-acid small fragment within S1 domain (residues 318-510) was identified as a receptor-binding domain (RBD), which is sufficient to associate with ACE2 (26-28).

The S proteins of coronaviruses are major antigenic determinants that induce the production of neutralizing antibodies (29, 30). Thus, it logically follows to use S protein as an antigen for vaccine development (30). Recently, it has been shown that the S protein of SARS-CoV is a major inducer of protective immunity among structural proteins (31). Yang, et al. (32) reported that a DNA vaccine candidate encoding the S protein induced SARS-CoV neutralization (neutralizing antibody titers ranged from 1:25 to 1:150) and protective immunity in mice, and it was proven that the protection was mediated by neutralizing antibodies but not by a T-cell-dependent mechanism. Bisht, et al. (33) demonstrated that the S protein of SARS-CoV expressed by attenuated vaccinia virus (MVA) elicited S-specific antibodies with SARS-CoV-neutralizing antibody titer of 1:284, and protectively-immunized mice against SARS-CoV infection as shown by reduced titers of SARS-CoV in the respiratory tracts of mice after the challenge infection. Bukreyev, et al. (34) reported that mucosal immunization of African green monkeys with an attenuated parainfluenza virus (BHPIV3) expressing the SARS-CoV S protein induced neutralizing antibodies with neutralization titers ranging from 1:8 to 1:16 and protected animals against the challenge infection. These data indicate that the S protein of SARS-CoV is a protective antigen capable of inducing neutralizing antibodies, although its antigenic determinants remain to be defined.

We have recently demonstrated that the receptor-binding domain (RBD) of SARS-CoV S protein is a major target of neutralizing antibodies induced in patients infected with SARS-CoV and in animals immunized with inactivated viruses or S proteins (35, 36). Therefore, we used the recombinant RBD of the SARS-CoV S protein as an immunogen to induce neutralizing monoclonal antibodies (mAbs).

BRIEF SUMMARY OF THE INVENTION

The present invention provides an isolated monoclonal antibody capable of binding to the receptor-binding domain (RBD) of the spike (S) protein of the severe acute respiratory syndrome-associated coronavirus (SARS-CoV) so as to competitively inhibit the binding of the SARS-CoV to host cells. Additionally, the present invention provides a substance comprising the complementary-determining regions of the monoclonal antibody described above, capable of binding to the same epitope as the monoclonal antibody described above.

In one embodiment, the substance described above is an antibody. In a preferred embodiment, said antibody is neutralizing. The present invention also provides for a single-chain antibody or antibody-fusion construct; a humanized antibody; and a chimeric antibody as described above.

It is the intention of the present application to cover different chimeric constructs created using the invented antibodies. The present invention also covers all the humanized constructs of the antibodies. In one embodiment, the isolated antibody described above is directly or indirectly coupled to cytotoxic agents.

The present invention also provides for cells which comprise the antibody. The present invention additionally provides a nucleic acid molecule encoding the above antibody. The present invention further provides a nucleic acid molecule capable of specifically hybridizing the molecule described above. The nucleic acid molecule includes, but is not limited to, synthetic DNA or RNA, genomic DNA, cDNA, and RNA.

The present invention also provides a vector comprising the above nucleic acid molecules or a portion thereof. In one embodiment, said vector is an expression vector, whereby the protein encoded by the above nucleic acid molecules may be expressed. This invention further comprises a cell which comprises the above-described nucleic acid molecules. Said cells may be used for expression.

The present invention provides a method for producing the antibody capable of binding to the receptor-binding domain (RBD) of the spike (S) protein of the SARS-CoV so as to competitively inhibit the binding of the SARS-CoV to host cells, comprising operatively-linking the nucleic acid molecule described above to the appropriate regulatory element so as to express said antibody; placing the linked nucleic molecule in appropriate conditions permitting the expression of said antibody; and recovery of said expressed antibody, thereby producing said antibody. This invention also provides an antibody produced by the above method.

The present invention provides a composition comprising an effective amount of the above-described monoclonal antibody and a suitable carrier. The present invention further provides a pharmaceutical composition comprising an effective amount of the above-described monoclonal antibody and a pharmaceutically-acceptable carrier.

The present invention also provides a method for treating infection of SARS-CoV using the above pharmaceutical composition. The present invention further provides a method for preventing infection of SARS-CoV using the above pharmaceutical composition.

The present invention also provides a method for detecting SARS-CoV (or the SARS-CoV-infected cells), comprising contacting the antibody or its derivative capable of binding the receptor-binding domain (RBD) of the spike (S) protein of said virus under conditions permitting the formation of complexes between the antibody, or its derivative, and the RBD of S protein of the SARS-CoV; and detecting the complexes formed.

Finally, the present invention provides a method for screening compounds capable of inhibiting infection of severe acute respiratory syndrome-associated coronavirus (SARS-CoV) by blocking the binding of said virus to receptors on host cells, comprising the steps of (a) establishing a system for the antibody to bind to the receptor-binding domain (RBD) of spike (S) protein of the SARS-CoV; and (b) contacting the compounds with the system of (a), whereby a decrease in binding of the above antibody to the RBD of S protein of the SARS-CoV indicates that the compounds are capable of interfering with said binding, thereby inhibiting infection of the RBD of S protein of the SARS-CoV. This invention further provides the resulting screened compounds. The compounds then can be used to treat or prevent severe acute respiratory syndrome (SARS).

The present invention provides a kit comprising a compartment containing an antibody capable of recognizing the SARS virus.

The present invention demonstrates that the receptor-binding domain (RBD) contains multiple, conformation-dependant, neutralization epitopes which induce a panel of potent neutralizing monoclonal antibodies (mAbs), which can be used for the treatment, diagnosis, and prevention of SARS.

BRIEF DESCRIPTION OF THE SEVERAL VIEWS OF THE DRAWINGS

FIG. 1. Epitope mapping of mAbs 4D5 and 17H9 by overlapping peptides that cover the RBD of S protein. Each of the peptides was coated at 5 μg/ml and mAbs were tested at 10 μg/ml.

FIG. 3. Neutralization of SARS pseudovirus by mAbs. Inhibition of SARS pseudovirus infection in 293T/ACE2 cells by representative mAbs from each group was shown. Each of the mAbs was tested at a series of 2-fold dilutions and % neutralization was calculated.

DETAILED DESCRIPTION OF THE INVENTION

Figure 2:
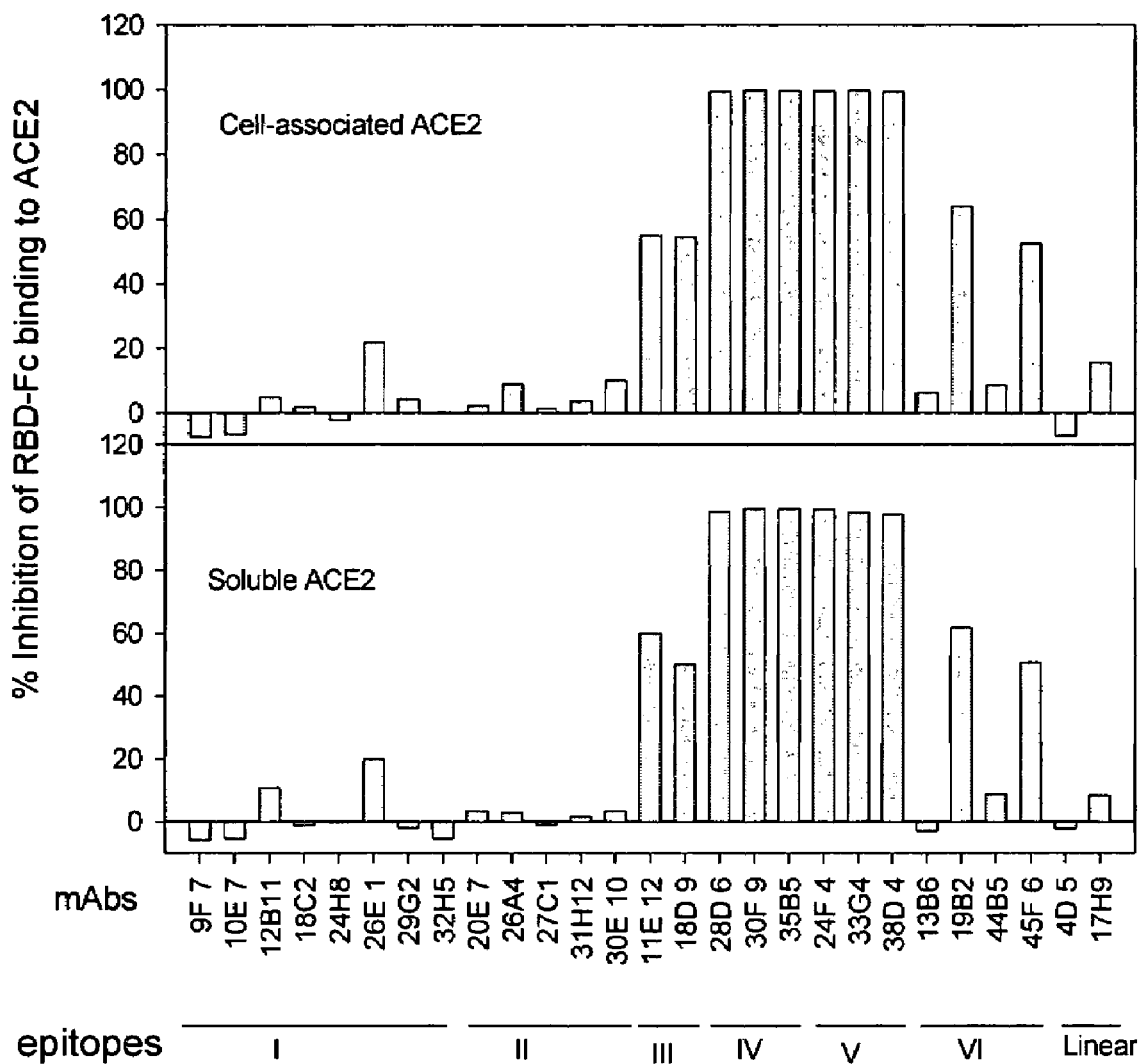
FIG. 2. Inhibition of RBD-Fc binding to ACE2 by mAbs. Upper panel shows inhibition of RBD-Fc binding to cell-associated ACE2 expressed on 293T/ACE2 cells measured by flow cytometry; lower panel shows inhibition of RBD-Fc binding to soluble ACE2 measure by ELISA. RBD-Fc was used at 1 μg/ml and mAbs were used at 50 μg/ml. % inhibition was calculated for each mAb.

The present invention provides an isolated monoclonal antibody capable of binding to receptor-binding domain (RBD) of the spike (S) protein of the severe acute respiratory syndrome-associated coronavirus (SARS-CoV) so as to competitively inhibit the binding of the SARS-CoV to host cells.

The present invention also provides a substance comprising the complementary-determining regions of the monoclonal antibody described above, capable of binding to the same epitope as the monoclonal antibody described above. This substance includes, but is not limited to, a polypeptide, small molecule, antibody, or a fragment of an antibody. In a preferred embodiment, the antibody is neutralizing. In another embodiment, the antibody is a single-chain antibody or antibody-fusion construct; a humanized antibody; or a chimeric antibody as described above. It is the intention of this application to cover different chimeric constructs created using the invented antibodies. The present invention also covers all the humanized constructs of the antibodies. The art of generating chimeric or humanized antibodies is well-known. See eg. (37, 38) for chimeric antibodies and (39-41) for humanized antibodies. An ordinarily-skilled artisan may modify the sequence of the above described substance in light of the present disclosure. Said modification may include addition, deletion, or mutation of certain amino acid sequences in the fragment. The general method to produce an antibody is within the knowledge of one of ordinary skill in the art. See e.g., Using Antibodies: A Laboratory Manual: Portable Protocol No. 1 by Ed. Harlow (1998).

In one embodiment, the isolated antibody described above is directly or indirectly coupled to one of more cytotoxic agent. Said cytotoxic agent includes, but is not limited to, radionucleotides or other toxins. The present invention also provides cells comprising the antibody. The present invention additionally provides a nucleic acid molecule encoding the above antibody. Once the antibodies are isolated, the gene which encodes said antibody may be isolated and the nucleic acid sequence will be determined. Accordingly, the present invention further provides a nucleic acid molecule capable of specifically hybridizing the molecule described above. The nucleic acid molecule includes, but is not limited to, synthetic DNA or RNA, genomic DNA, cDNA, and RNA.

The present invention also provides a vector comprising the above nucleic acid molecules or a portion thereof. This portion may be a functional portion which carries out a certain function. A fragment or a partial sequence may be able to encode a functional domain of the protein which is functional. In one embodiment, this vector is an expression vector, whereby the protein encoded by nucleic acid molecule may be expressed. The present invention further provides a cell comprising the above-described nucleic acid molecule. Said cells may be used for expression. Vectors are well-known in this field. See e.g., Graupner, U.S. Pat. No. 6,337,208, "Cloning Vector," issued Jan. 8, 2002. See also, Schumacher et. al., U.S. Pat. No. 6,190,906, "Expression Vector for the Regulatable Expression of Foreign Genes in Prokaryotes," issued Feb. 20, 2001. In one embodiment, the vectors are plasmids.

The present invention provides a method for producing the antibody capable of binding to receptor-binding domain (RBD) of the spike (S) protein of the SARS-CoV so as to competitively inhibit the binding of the SARS-CoV to host cells, comprising operatively-linking the nucleic acid molecule described above to appropriate regulatory element so as to express said antibody; placing the linked nucleic molecule in appropriate conditions permitting the expression of said antibody; and recovery of said expressed antibody, thereby producing said antibody. The present invention also provides an antibody produced by the above method.

Hybridoma cell lines 32H5 (Conf I), 31H12 (Conf II), 18D9 (Conf III), 30F9 (Conf IV), 33G4 (Conf V), and 19B2 (Conf VI) were deposited on Jan. 13, 2005 with American Type Culture Collection (ATCC), 10801 University Blvd., Manassas, Va. 20110, U.S.A., under the provisions of the Budapest Treaty for the International Recognition of the Deposit of Microorganism for the Purposes of Patent Procedure. Cell lines 32H5 (Conf I), 31H12 (Conf II), 18D9 (Conf III), 30F9 (Conf IV), 33G4 (Conf V), and 19B2 (Conf VI) were accorded ATCC Accession Numbers PTA-6525, PTA-6524, PTA-6521, PTA-6523, PTA-6526, and PTA-6522, respectively.

The present invention also provides epitopes recognized by the above-described monoclonal antibodies. Said epitopes, sequential or conformational, are important for diagnostic or therapeutic uses.

The present invention provides a composition comprising an effective amount of the above-described monoclonal antibody and a suitable carrier. The effective amount may be determined by routine experimentation. The present invention additionally provides a pharmaceutical composition comprising an effective amount of the above-described monoclonal antibody and a pharmaceutically-acceptable carrier. As used herein, a pharmaceutically-acceptable carrier means any of the standard pharmaceutical carriers. Examples of suitable carriers are well-known in the art and may include, but are not limited to, any of the standard pharmaceutical carriers such as a phosphate buffered saline solutions, phosphate buffered saline containing Polysorb 80, water, emulsions such as oil/water emulsion, and various types of wetting agents. Other carriers may also include sterile solutions, tablets, coated tablets, and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The present invention also provides a method for treating infection of SARS-CoV using the above pharmaceutical composition. The present invention additionally provides a method for preventing infection of SARS-CoV using the above pharmaceutical composition. The present invention further provides a method for detecting SARS-CoV (or the SARS-CoV-infected cells), comprising contacting the antibody, or its derivative, capable of binding to the receptor-binding domain (RBD) of the spike (S) protein of said virus under conditions permitting the formation of complexes between the antibody, or its derivative, and the RBD of the S protein of the SARS-CoV; and detecting the complexes formed.

Finally, the present invention provides a method for screening compounds capable of inhibiting infection of SARS-CoV by blocking the binding of said virus to receptors on host cells, comprising the steps of (a) establishing a system for the antibody to bind to the receptor-binding domain (RBD) of the spike (S) protein of the SARS-CoV; and (b) contacting the compounds with the system of (a), whereby a decrease in binding of the above antibody to the RBD of the S protein of the SARS-CoV indicates that the compounds are capable of interfering with said binding, thereby inhibiting infection of the RBD of the S protein of the SARS-CoV. The present invention further provides the resulting screened compounds, which can be used to treat or prevent severe acute respiratory syndrome (SARS).

The present invention provides a kit comprising a compartment containing an antibody capable of recognizing the SARS virus and/or a substance which can competitively inhibit the binding of said antibody.

The present invention demonstrates that the RBD contains multiple conformation-dependant neutralization epitopes which induce a panel of potent neutralizing monoclonal antibodies (mAbs), which can be used for the treatment, diagnosis and prevention of SARS.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

Twenty-seven hybridoma clones were generated by fusing SP2/0 myeloma cells with the splenocytes from Balb/c mice immunized with a fusion protein containing a receptor-binding domain (RBD) in the spike (S) protein of the SARS-CoV linked to human IgG1 Fc fragment (designated RBD-Fc). Among the 27 monoclonal antibodies (mAbs) produced from these hybridoma clones, except 2 mAbs bound to the adjacent linear epitopes, all other mAbs recognized conformation-dependant epitopes. Based on the results obtained from binding competition experiments, these 25 conformation-specific mAbs could be divided into six groups, designated as Conf I-VI. The Conf IV and Conf V mAbs significantly blocked RBD-Fc binding to ACE2, the receptor for SARS-CoV, suggesting that their epitopes overlap with the receptor-binding sites in the S protein. Most of the mAbs (23/25) that recognize the conformational epitopes possessed potent neutralizing activities against SARS pseudovirus with 50% neutralizing dose ($ND_{50}$) raging from 0.005 to 6.569 µg/ml.

These SARS-CoV neutralizing mAbs can be used: 1) as immunotherapeutics for early treatment of SARS-CoV infection; 2) as biological reagents for diagnosis of SARS-CoV infection; and 3) as probes for studying the immunogenicity, antigenicity, structure and function of the SARS-CoV S protein. Furthermore, these murine mAbs can be humanized for therapy and prevention of SARS-CoV infection.

Materials and Methods

Immunization of mice and generation of mAbs. Five Balb/c mice (4 wks old) were immunized subcutaneously with 20 µg of Protein A Sepharose-purified RBD-Fc prepared as previously described (35) in the presence of MLP+TDM Adjuvant System (Sigma, Saint Louis, Mich.) and boosted with 10 µg of the same antigen plus the MLP+TDM adjuvant at 3-wk intervals. Mouse antisera were collected for detecting anti-RBD antibodies and SARS-CoV-neutralizing antibodies.

Hybridomas for producing anti-RBD mAbs were generated using standard protocol. Briefly, the splenocytes from the immunized mice were harvested and fused with SP2/0 myeloma cells. Cell culture supernatants from the wells containing hybridoma colonies were screened by enzyme-linked immunosorbent assay (ELISA) using S1-C9 prepared as previously described (35) as a coating antigen. Cells from positive wells were expanded and retested. Cultures that remained positive were subcloned to generate stable hybridoma cell lines. All mAbs were purified from culture supernatants by Protein A Sepharose 4 Fast Flow (Amersham Biosciences).

ELISA and binding competition. Reactivity of mouse sera or mAbs with various antigens was determined by ELISA. Briefly, 1 μg/ml recombinant proteins (RBD-Fc or S1-C9) or purified human IgG (Zymed, South San Francisco, Calif.) were used, respectively, to coat 96-well microtiter plates (Corning Costar, Acton, Mass.) in 0.1 M carbonate buffer (pH 9.6) at 4° C. overnight. After blocking with 2% non-fat milk, serially diluted mouse sera or mAbs were added and incubated at 37° C. for 1 h, followed by four washes with PBS containing 0.1% Tween 20. Bound antibodies were detected with HRP-conjugated goat anti-mouse IgG (Zymed) at 37° C. for 1 h, followed by washes. The reaction was visualized by addition of the substrate 3,3',5,5'-tetramethylbenzidine (TMB) and absorbance at 450 nm was measured by an ELISA plate reader (Tecan US, Research Triangle Park, N.C.).

To determine the effect of disulfide bond reduction on the binding of RBD-specific mAbs, ELISA plate was coated with recombinant RBD-Fc or S1-C9 at a concentration of 1 μg/ml and then treated for 1 h at 37° C. with dithiothreitol (DTT) at a concentration of 10 mM, followed by washes. Then the wells were treated with 50 mM iodoacetamide for 1 h at 37° C. After washes, a standard ELISA was performed as described above.

A competitive ELISA was performed to determine the inhibitory activity of the RBD-specific mAbs on binding of the biotinylated mAbs to RBD-Fc. Briefly, the wells of ELISA plates were coated with RBD-Fc at 1 μg/ml as described above. A mixture containing 50 μg/ml of an unlabeled mAb and 1 μg/ml of a biotinylated mAb was added, followed by incubation at 37° C. for 1 h. Binding of the biotinylated mAbs was detected after addition of HRP-conjugated streptavidin (Zymed) and TMB sequentially. Biotinylation of mAbs was performed using the EZ-link NHS-PEO Solid Phase Biotinylation Kit (Pierce, Rockford, Ill.) according to the manufacturer's protocol.

Neutralization of SARS pseudovirus infection. The conventional neutralization assay using live SARS-CoV is cumbersome and has to be performed in BSL-3 facilities. We therefore adapted a SARS-CoV pseudovirus system (27, 32, 42, 43) in our laboratory. This assay is sensitive and quantitative and can be carried out in BSL-2 facilities. SARS pseudovirus bearing SARS-CoV S protein and a defective HIV-1 genome that expresses luciferase as reporter was prepared as previously described (27, 42, 43). In brief, 293T cells were co-transfected with a plasmid encoding codon-optimized SARS-CoV S protein and a plasmid encoding Env-defective, luciferase-expressing HIV-1 genome (pNL4-3.luc.RE) using Fugene 6 reagents (Boehringer Mannheim). Supernatants containing SARS pseudovirus were harvested 48 hours post-transfection and used for single-cycle infection of ACE2-transfected 293T (293T/ACE2) cells. Briefly, 293T/ACE2 cells were plated at $10^4$ cells/well in 96-well tissue-culture plates and grown overnight. The supernatants containing pseudovirus were preincubated with 2-fold serially diluted mouse sera or mAbs at 37° C. for 1 h before addition to cells. The culture was re-fed with fresh medium 24 h later and incubated for an additional 48 h. Cells were washed with PBS and lysed using lysis reagent included in a luciferase kit (Promega, Madison, Wis.). Aliquots of cell lysates were transferred to 96-well Costar flat-bottom luminometer plates (Corning Costar, Corning, N.Y.), followed by addition of luciferase substrate (Promega). Relative light units (RLU) were determined immediately in the Ultra 384 luminometer (Tecan US).

Binding inhibition of RBD-Fc with receptor by mAbs. Inhibition of mAbs on RBD-Fc binding to ACE2-expressing cells was measured by flow cytometry. Briefly, $10^6$ 293T/ACE2 cells were detached, collected, and washed with Hank's balanced salt solution (HBSS) (Sigma, St. Louis, Mo.). RBD-Fc was added to the cells to a final concentration of 1 μg/ml in the presence or absence of 50 μg/ml mAbs, followed by incubation at room temperature for 30 min. Cells were washed with HBSS and incubated with anti-human IgG-FITC conjugate (Zymed) at 1:50 dilution at room temperature for an additional 30 min. After washing, cells were fixed with 1% formaldehyde in PBS and analyzed in a Becton FACSCalibur flow cytometer (Mountain View, Calif.) using CellQuest software.

Inhibition of RBD-Fc binding to soluble ACE2 by mAbs was measured by ELISA. Briefly, recombinant soluble ACE2 (R&D systems, Inc., Minneapolis, Minn.) at 2 μg/ml was coated onto 96-well ELISA plates (Corning Costar) in 0.1 M carbonate buffer (pH 9.6) at 4° C. overnight. After blocking with 2% non-fat milk, 1 μg/ml RBD-Fc was added to the wells in the presence or absence of 50 μg/ml mouse mAbs and incubated at 37° C. for 1 hour. After washing, the HRP-conjugated goat anti-human IgG (Zymed) was added and incubated an additional 1 h. After washing, the substrate TMB was used for detection.

Results

Isolation and initial characterization of mAbs specific for RBD. RBD-Fc fusion protein was transiently expressed in 293T cells and purified to homogenicity by Protein A. Five mice (A to E) were immunized four times with RBD-Fc in the presence of Ribi adjuvant. All animals developed appreciable antibody responses against RBD-Fc after the first boost, and their antibody titers increased with subsequent immunizations. The antisera collected 4 days after the third boost showed highly potent neutralizing activity against SARS-CoV and SARS pseudovirus bearing SARS-CoV S protein.

A panel of 27 RBD-specific mAbs was generated by fusing splenocytes from the RBD-Fc-immunized mice with Sp2/0 myeloma cells and then screening hybridomas with S1-C9 as an antigen. Epitope specificities of these mAbs were initially determined by ELISAs using RBD-Fc, DTT-reduced RBD-Fc, S1-C9, DTT-reduced S1-C9, and a purified human IgG as coating antigens (Table I). Majority of the mAbs (25/27) were reactive with native RBD-Fc and S1-C9, but not DTT-reduced RBD-Fc and S1-C9. This indicated that they were directed against disulfide bond-dependent conformational epitopes expressed on the RBD of S protein. Other two mAbs (4D5 and 17H9) recognized both native and reduced RBD-Fc and S1-C9, indicating that they were directed against linear epitopes presented on the RBD. None of the mAbs screened by S1-C9 reacted with human IgG, whereas control antiserum from a mouse immunized with RBD-Fc was reactive with human IgG (Table I).

Figure 1:
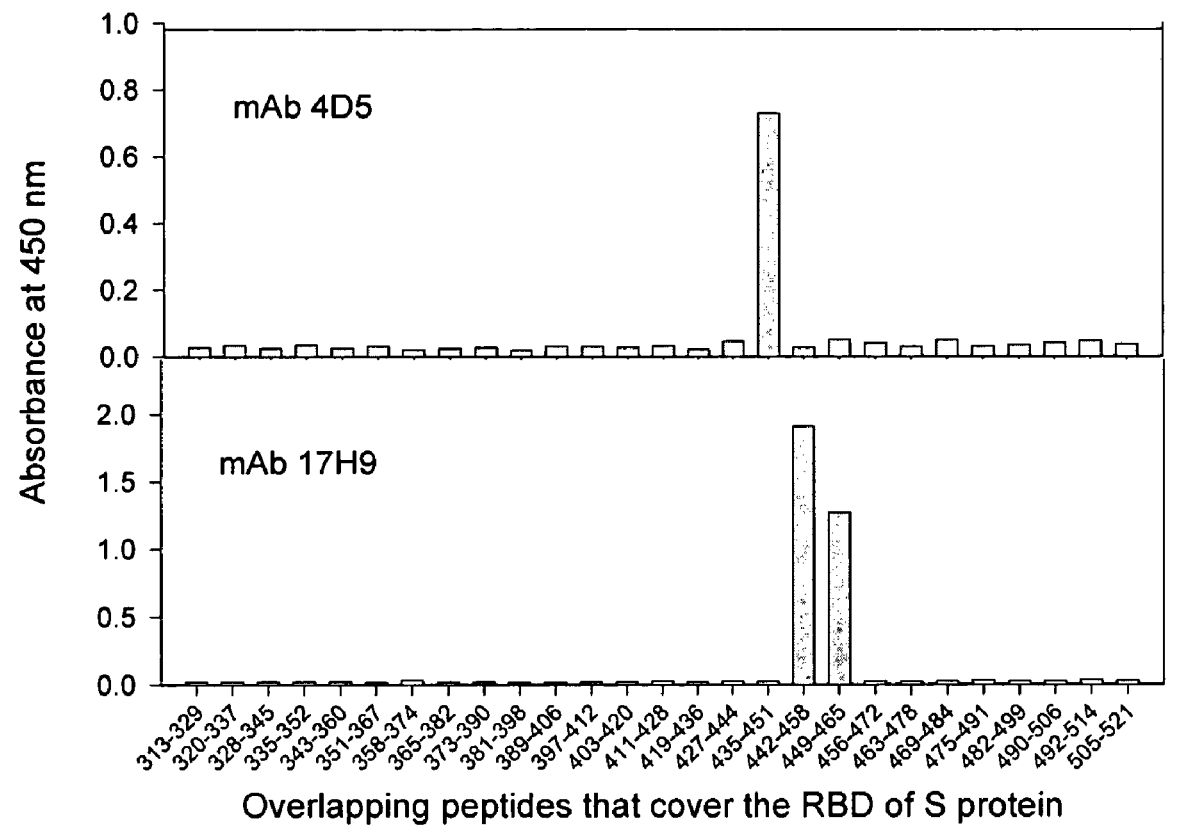

Since the mAbs 4D5 and 17H9 could react with the reduced RBD-Fc and S1-C9, their epitopes might be mapped with synthetic peptides. A set of 27 overlapping peptides that cover the RBD of S protein was used to localize 4D5 and 17H9 epitopes by ELISA. As shown in FIG. 1, 4D5 reacted with the peptide 435-451 (NYNYKYRYLRHGKLRPF, SEQ ID NO:1), and 17H9 reacted with two overlapped peptides 442-458 (YLRHGKLRPFERDISNV, SEQ ID NO:2) and 449-465 (RPFERDISNVPFSPDGK, SEQ ID NO:3). While the epitope of 17H9 was clearly mapped to the overlapped sequence (RPFERDISNV, SEQ ID NO:4) of the peptides 442-458 and 449-465, the epitope for 4D5 requires most sequence of the peptide 435-451 which overlaps partial sequences of the peptides 442-458 and 449-465. Therefore, these two mAbs recognize neighboring linear epitopes that reside within the RBD. None of the conformation-dependant mAbs reacted with any of the tested peptides (data not shown).

Epitope specificity of the RBD-specific mAbs determined by binding competition assays. In order to characterize the conformation-dependant epitopes, the RBD-specific mAbs were grouped by binding competition assays (Table II). One of the mAbs (10E7) was first biotinylated and the inhibitory activity of the 27 mAbs on 10E7 binding to RBD-Fc was measured. The mAbs 4D5 and 17H9 recognizing linear epitopes mapped by peptides above were included in the competition assays as a control. About half of the conformation-dependant mAbs (13/25) competed with biotinylated 10E7, while other mAbs did not block 10E7 binding to RBD-Fc. Another four of the non-competing mAbs (11 E12, 33G4, 45B5, and 17H9) were subsequently biotinylated and tested similarly with the binding competition assay. Five of the 13 mAbs that compete with the biotinylated 10E7 also blocked the biotinylated 45B5 binding to RBD-Fc and were designated as a separate group. Thus, the 25 conformation-specific mAbs were divided into six distinct competition groups (designated as Conf I-VI). Two linear epitope-specific mAbs (4D5 and 17H9) did not compete with any of conformation-specific mAbs. These results suggest that the RBD of S protein contains multiple antigenic structures that induce specific antibody responses in the mice. However, the immunodominant epitopes in the RBD are conformation-dependant.

Characterization of the mAbs that block receptor binding. RBD-Fc could efficiently bind to ACE2 expressed on 293T/ACE2 cells and to soluble ACE2 as measured by flow-cytometry and ELISA, respectively (data not shown). We tested whether the RBD-specific mAbs inhibit binding of RBD-Fc to cell-associated or soluble ACE2. As shown in FIG. 2, all of the mAbs from Conf IV (28D6, 30F9, and 35B5) and Conf V (24F4, 33G4, and 38D4) completely blocked RBD-Fc binding to both cell-associated and soluble ACE2 in a highly consistent manner. All the two Conf III mAbs (11E12 and 18D9) and two of the four Conf VI mAbs (19B2 and 45F6) partially inhibited RBD-Fc binding to ACE2 expressed on 293T/AEC2 cells and soluble ACE2. All of other mAbs, including two mAbs against linear sequences, had no significant inhibitory effects on receptor binding. These results indicate that the Conf IV and Conf V mAbs recognize epitopes that may overlap with the conformational receptor-binding sites in the S protein, although these mAbs did not compete against each other in the binding competition assays. Conf III mAbs and two Conf VI mAbs (19B2 and 45F6) may also bind to the conformational epitopes being involved in the receptor-binding. All the Conf I and Conf II mAbs did not block the receptor binding, suggesting that they recognize the conformational epitopes that do not overlap the receptor-binding sites in RBD. These results highlight the epitopic heterogenecity of the RBD-specific mAbs and further indicate that the RBD of S protein contains multiple antigenic conformations.

RBD-specific mAbs have potent neutralizing activity. Each of the RBD-specific mAbs was tested for neutralizing activity against SARS pseudovirus. Strikingly, the majority of the conformation-dependant mAbs (23/25) had potent neutralizing activity with 50% neutralization dose ($ND_{50}$) ranging from 0.005 to 6.569 μg/ml (Table III), whereas two mAbs that direct against linear epitopes (4D5 and 17H9) and one mAb from Conf VI (44B5) at a concentration as high as 100 μg/ml did not neutralize the SARS pseudovirus infection. The mAbs 33G4 from Conf V and 30F9 from Conf IV that blocked the receptor binding had highest neutralizing activities against the pseudovirus. Interestingly, even 45F6 from Conf VI, with its relatively lower pseudovirus neutralization activity, partially blocked the binding of RBD-Fc with ACE2. The dose-dependent neutralizing activity of several representative mAbs from each of groups was presented in FIG. 3. These results suggest that the RBD of S protein predominantly induce neutralizing antibodies that direct against conformational epitopes.

EXPERIMENTAL DISCUSSION

Recent studies have shown that the S protein of SARS-CoV is one of the major antigens eliciting immune responses during infection (44-46). These suggest that the S protein may serve as an immunogen for inducing neutralizing mAbs. In the present study, we used a recombinant fusion protein RBD-Fc as an immunogen to immunize mice and generated hybridoma clones to produce 27 mAbs. A majority of these mAbs (25/27) recognized conformational epitopes and among them, 23 mAbs had potent neutralizing activity. Only two mAbs were mapped to adjacent linear epitopes by overlapping peptides and they could not neutralize infection by SARS pseudovirus. Interestingly, the conformation-dependant mAbs could be divided into six different groups (i.e., Conf I-VI) based on a binding competition experiment, suggesting that there are several distinct conformational epitopes on the RBD that can elicit neutralizing antibodies.

It is expected that all the neutralizing mAbs directed against the RBD can block the interaction between RBD and ACE2, the functional receptor for SARS-CoV. However, we found that only the mAbs recognizing the Conf IV and V could efficiently block RBD binding to ACE2. Some mAbs reacting with the Conf III and VI partially inhibited interaction between the RBD and ACE2. This suggests that their epitopes may overlap the receptor-binding sites on the RBD or binding of these mAbs to RBD may cause conformational change of the receptor binding sites, resulting in inhibition of RBD binding to ACE2. The mAbs that recognize the Conf I and II did not significantly affect the RBD binding with ACE2, but also possessed potent neutralizing activities, suggesting that these mAbs inhibit SARS-CoV infection without interfering in RBD-ACE2 interaction. The mechanism of action of these mAbs needs to be further investigated. These data indicate that the RBD induces neutralizing antibodies specific not only for the receptor-binding sites, but also for other unique structural conformations, highlighting its antigenic heterogenicity, and suggest that the RBD of SARS-CoV S protein contains multiple conformational epitopes responsible for induction of potent neutralizing antibody responses.

The conformational sensitivity of the SARS-CoV neutralizing mAbs described here is consistent with properties of neutralizing mAbs raised against other enveloped viruses, which generally require more native conformation for binding (47, 48). Although the RBD of SARS-CoV S protein is a 193-amino-acid small fragment, it contains seven cysteines and five of which are essential for ACE2 association. The disulfide-bonds between these cysteines may form complex tertiary structures to constitute the multiple antigenic conformations. However, a neutralizing human mAb selected from a nonimmune human antibody library could react with the DTT-reduced S protein and block receptor association (49). Therefore, further characterization is needed to define the neutralization determinants on the RBD of SARS-CoV S protein, and this may provide critical information for developing anti-SARS therapeutics and vaccines.

It was reported that passive transfer of mouse immune sera reduced pulmonary viral replication in the mice challenged with SARS-CoV (33, 50), and prophylactic administration of neutralizing mAbs conferred in vivo protection in the mice or in the ferrets (51, 52), suggesting that passive immunization with anti-SARS antibodies is a viable strategy to control SARS. Thus, mAbs with high levels of SARS-CoV neutralizing activity may be used for early treatment of SARS-CoV infection. However, application of murine MAbs in human will be limited due to human-anti-mouse antibody (HAMA) responses (53-55). If only a few doses of murine mAbs are used in a short period of time (one to two weeks) at the early stage of SARS-CoV infection may not cause serious HAMA, but this urgent treatment may save lives of SARS patients. We have used similar strategies for early treatment of Hantaan virus (HTNV) infection using murine anti-HTNV mAbs(56). Furthermore, the murine neutralizing mAbs can be humanized as therapeutics or immunoprophylaxis for providing immediate protection against SARS-CoV infection to those at-risk populations.

The significance of the present study is three-fold. First, a number of highly potent RBD-specific neutralizing mAbs have been generated, which may be developed as immunotherapeutics for urgent SARS treatment. Second, these mAbs can be developed as diagnostic agents for detecting SARS-CoV infection. Third, these mAbs can be used as probes for studying the immunogenicity, antigenicity, structure, and function of the SARS-CoV S protein. These mAbs can be further humanized for treatment and prevention of SARS.

TABLE I

Reactivities of RBD-specific mAbs against various antigens[a]

| mAbs | Isotype | RBD-Fc | Reduced RBD-Fc | S1-C9 | Reduced S1-C9 | Human IgG |
|---|---|---|---|---|---|---|
| 4D5 | IgG1/K | 0.88 | 1.36 | 0.65 | 0.94 | 0.02 |
| 9F7 | IgG1/K | 1.60 | 0.00 | 1.45 | 0.08 | 0.04 |
| 10E7 | IgG1/K | 1.77 | 0.02 | 1.72 | 0.16 | 0.05 |
| 11E12 | IgG2a/K | 1.50 | 0.01 | 0.72 | 0.09 | 0.02 |
| 12B11 | IgG1/K | 1.37 | 0.04 | 0.78 | 0.00 | -0.01 |
| 13B6 | IgG1/K | 1.58 | -0.01 | 0.93 | 0.00 | 0.02 |
| 17H9 | IgG1/K | 1.72 | 1.71 | 1.21 | 1.15 | 0.07 |
| 18C2 | IgG1/K | 1.28 | -0.01 | 0.80 | 0.01 | -0.20 |
| 18D9 | IgG1/K | 1.47 | -0.01 | 0.90 | 0.01 | 0.03 |
| 19B2 | IgG1/K | 1.63 | 0.00 | 1.55 | 0.12 | 0.01 |
| 20E7 | IgG2a/K | 1.50 | 0.00 | 0.98 | 0.01 | 0.02 |
| 24F4 | IgG1/K | 1.69 | -0.01 | 1.08 | 0.08 | 0.04 |
| 24H8 | IgG1/K | 1.54 | -0.01 | 0.94 | 0.12 | 0.01 |
| 26A4 | IgG1/K | 1.60 | 0.00 | 0.89 | 0.09 | 0.01 |
| 26E1 | IgG1/K | 1.91 | 0.07 | 1.85 | 0.06 | 0.01 |
| 27C1 | IgG1/K | 1.46 | 0.00 | 1.57 | 0.07 | 0.01 |
| 28D6 | IgG1/K | 2.06 | 0.01 | 1.60 | 0.16 | 0.00 |
| 29G2 | IgG2a/K | 1.69 | 0.00 | 0.96 | 0.17 | 0.04 |
| 30F9 | IgG1/K | 1.66 | 0.04 | 1.21 | 0.12 | 0.01 |
| 31H12 | IgG1/K | 1.72 | 0.08 | 1.91 | 0.22 | 0.03 |
| 32H5 | IgG1/K | 1.54 | 0.06 | 1.55 | 0.51 | 0.00 |
| 33G4 | IgG2a/K | 1.79 | 0.02 | 1.76 | 0.20 | -0.01 |
| 34E10 | IgG1/K | 1.62 | 0.10 | 1.82 | 0.18 | 0.04 |
| 35B5 | IgG1/K | 1.74 | 0.06 | 1.72 | 0.25 | 0.02 |
| 38D4 | IgG1/K | 1.63 | -0.01 | 1.20 | 0.07 | 0.00 |

TABLE I-continued

Reactivities of RBD-specific mAbs against various antigens[a]

| mAbs | Isotype | RBD-Fc | Reduced RBD-Fc | S1-C9 | Reduced S1-C9 | Human IgG |
|---|---|---|---|---|---|---|
| 44B5 | IgG1/K | 1.57 | 0.09 | 1.64 | 0.16 | 0.00 |
| 45F6 | IgG1/K | 1.61 | 0.11 | 1.43 | 0.15 | -0.01 |
| Antiserum | | 2.22 | 1.78 | 2.32 | 1.68 | 2.07 |
| Naïve serum | | 0.01 | 0.02 | 0.02 | 0.01 | 0.04 |

[a]Antigens were used at 1 μg/ml; mAbs were tested at 10 μg/ml and sera were tested at 1:100 dilution.
Positive reactivities are highlighted in boldface.

TABLE II

% Inhibition of RBD-specific mAbs on binding of biotinylated mAbs to RBD-Fc[a]

| Group | Competing mAb | Biotinylated mAb | | | | |
|---|---|---|---|---|---|---|
| | | 10 E7 | 11 E12 | 33G4 | 45B5 | 17H9 |
| Conf I | 9F7 | 84.5 | 11.7 | -13.3 | 22.3 | 16.4 |
| | 10E 7 | 91.0 | 5.6 | -12.9 | 21.0 | 9.9 |
| | 12B11 | 85.8 | 19.3 | -0.2 | 19.8 | 21.0 |
| | 18C2 | 84.9 | 19.3 | 4.9 | 18.1 | 19.4 |
| | 24H8 | 93.7 | 24.0 | 7.0 | 25.6 | 22.1 |
| | 26E1 | 95.1 | 10.5 | 37.4 | 30.4 | 25.0 |
| | 29G2 | 96.6 | 20.4 | 1.6 | 11.4 | 23.5 |
| | 32H5 | 98.9 | 18.5 | 4.4 | 9.1 | 20.3 |
| Conf II | 20E7 | 97.2 | 38.5 | 5.9 | 73.0 | 24.6 |
| | 26A4 | 96.3 | 33.1 | -0.5 | 60.0 | 19.0 |
| | 27C1 | 97.2 | 36.7 | 14.6 | 73.7 | 20.9 |
| | 31H12 | 97.5 | 18.7 | 7.1 | 58.4 | 19.7 |
| | 30E10 | 98.3 | 19.3 | 12.9 | 68.9 | 24.6 |
| Conf III | 11E12 | 12.6 | 92.0 | 0.3 | -3.7 | 20.2 |
| | 18D9 | -16.2 | 98.3 | 8.3 | 23.6 | 17.1 |
| Conf IV | 28D6 | 39.7 | 99.6 | 13.8 | 67.4 | 26.6 |
| | 30F9 | 28.7 | 100.0 | 8.7 | 64.0 | 32.4 |
| | 35B5 | 34.9 | 99.9 | 10.0 | 64.7 | 33.6 |
| Conf V | 24F4 | 11.5 | -1.0 | 95.5 | 2.5 | 24.9 |
| | 33G4 | 9.5 | -3.7 | 99.5 | 26.4 | 29.1 |
| | 38D4 | 8.1 | -14.4 | 82.0 | -5.1 | 15.8 |
| Conf VI | 13B6 | 23.3 | 10.7 | -4.9 | 72.5 | 12.6 |
| | 19B2 | 2.9 | -26.4 | 18.0 | 50.0 | 16.1 |
| | 44B5 | 25.3 | -20.6 | 10.0 | 95.6 | 19.4 |
| | 45F6 | 25.7 | -10.4 | 10.8 | 94.8 | 23.5 |
| Linear | 4D5 | 13.0 | 10.6 | -11.1 | 1.0 | -10.5 |
| | 17H9 | 17.8 | 33.3 | -5.8 | 25.0 | 97.8 |

[a]Competing mAbs were tested at 100 μg/ml for the ability to block binding of the biotinylated mAbs to the RBD-Fc in ELISA. Greater than 40% inhibition was considered positive competition (values in bold).
Negative numbers indicate increased binding of the biotinylated reagent.

TABLE III

Neutralization activity of RBD-specific mAbs against SARS pseudovirus

| Group | mAb | Inhibition of ACE2 binding[a] | ND$_{50}$ (μg/ml) |
|---|---|---|---|
| Conf I | 9F7 | – | 6.569 |
| | 10E 7 | – | 1.673 |
| | 12B11 | – | 4.918 |
| | 18C2 | – | 5.031 |
| | 24H8 | – | 3.955 |
| | 26E1 | – | 0.354 |
| | 29G2 | – | 3.02 |
| | 32H5 | – | 0.275 |

TABLE III-continued

Neutralization activity of RBD-specific mAbs against SARS pseudovirus

| Group | mAb | Inhibition of ACE2 binding[a] | ND$_{50}$ (µg/ml) |
|---|---|---|---|
| Conf II | 20E7 | − | 5.959 |
| | 26A4 | − | 2.815 |
| | 27C1 | − | 1.607 |
| | 31H12 | − | 0.139 |
| | 30E10 | − | 0.399 |
| Conf III | 11E12 | + | 1.39 |
| | 18D9 | + | 0.02 |
| Conf IV | 28D6 | ++ | 0.298 |
| | 30F9 | ++ | 0.009 |
| | 35B5 | ++ | 0.131 |
| Conf V | 24F4 | ++ | 0.052 |
| | 33G4 | ++ | 0.005 |
| | 38D4 | ++ | 0.332 |
| Conf VI | 13B6 | − | 1.436 |
| | 19B2 | + | 0.936 |
| | 44B5 | − | >100 |
| | 45F6 | + | 43.894 |
| Linear | 4D5 | − | >100 |
| | 17H9 | − | >100 |

[a] "−," "+," and "++" indicate no, partial, and complete inhibition, respectively.

REFERENCES

1. Drosten, C., S. Gunther, W. Preiser, W. S. Van Der, H. R. Brodt, S. Becker, H. Rabenau, M. Panning, L. Kolesnikova, R. A. Fouchier, A. Berger, A. M. Burguiere, J. Cinatl, M. Eickmann, N. Escriou, K. Grywna, S. Kramme, J. C. Manuguerra, S. Muller, V. Rickerts, M. Sturmer, S. Vieth, H. D. Klenk, A. D. Osterhaus, H. Schmitz, and H. W. Doerr. 2003. Identification of a novel coronavirus in patients with severe acute respiratory syndrome. *N. Engl. J. Med.* 348:1967-1976.
2. Ksiazek, T. G., D. Erdman, C. S. Goldsmith, S. R. Zaki, T. Peret, S. Emery, S. Tong, C. Urbani, J. A. Comer, W. Lim, P. E. Rollin, S. F. Dowell, A. E. Ling, C. D. Humphrey, W. J. Shieh, J. Guarner, C. D. Paddock, P. Rota, B. Fields, J. DeRisi, J. Y. Yang, N. Cox, J. M. Hughes, J. W. LeDuc, W. J. Bellini, and L. J. Anderson. 2003. A novel coronavirus associated with severe acute respiratory syndrome. *N. Engl. J. Med.* 348:1953-1966.
3. Peiris, J. S., S. T. Lai, L. L. Poon, Y. Guan, L. Y. Yam, W. Lim, J. Nicholls, W. K. Yee, W. W. Yan, M. T. Cheung, V. C. Cheng, K. H. Chan, D. N. Tsang, R. W. Yung, T. K. Ng, and K. Y. Yuen. 2003. Coronavirus as a possible cause of severe acute respiratory syndrome. *Lancet* 361:1319-1325.
4. Marra, M. A., S. J. M. Jones, C. R. Astell, R. A. Holt, A. Brooks-Wilson, Y. S. N. Butterfield, J. Khattra, J. K. Asano, S. A. Barber, S. Y. Chan, A. Cloutier, S. M. Coughlin, D. Freeman, N. Girn, O. L. Griffith, S. R. Leach, M. Mayo, H. McDonald, S. B. Montgomery, P. K. Pandoh, A. S. Petrescu, A. G. Robertson, J. E. Schein, A. Siddiqui, D. E. Smailus, J. M. Stott, G. S. Yang, F. Plummer, A. Andonov, H. Artsob, N. Bastien, K. Bernard, T. F. Booth, D. Bowness, M. Czub, M. Drebot, L. Fernando, R. Flick, M. Garbutt, M. Gray, A. Grolla, S. Jones, H. Feldmann, A. Meyers, A. Kabani, Y. Li, S. Normand, U. Stroher, G. A. Tipples, S. Tyler, R. Vogrig, D. Ward, B. Watson, R. C. Brunham, M. Krajden, M. Petric, D. M. Skowronski, C. Upton, and R. L. Roper. 2003. The genome sequence of the SARS-associated coronavirus. *Science* 300:1399-1404.
5. Rota, P. A., M. S. Oberste, S. S. Monroe, W. A. Nix, R. Campagnoli, J. P. Icenogle, S. Penaranda, B. Bankamp, K. Maher, M. H. Chen, S. Tong, A. Tamin, L. Lowe, M. Frace, J. L. DeRisi, Q. Chen, D. Wang, D. D. Erdman, T. C. T. Peret, C. Burns, T. G. Ksiazek, P. E. Rollin, A. Sanchez, S. Liffick, B. Holloway, J. Limor, K. McCaustland, M. Olsen-Rasmussen, R. Fouchier, S. Gunther, A. D. M. E. Osterhaus, C. Drosten, M. A. Pallansch, L. J. Anderson, and W. J. Bellini. 2003. Characterization of a Novel Coronavirus Associated with Severe Acute Respiratory Syndrome. *Science* 300:1394-1399.
6. Fleck, F. 2004. SARS virus returns to China as scientists race to find effective vaccine. *Bull. World Health Organ.* 82:152-153.
7. Marshall, E. and M. Enserink. 2004. Medicine. Caution urged on SARS vaccines. *Science* 303:944-946.
8. Peiris, J. S., Y. Guan, and K. Y. Yuen. 2004. Severe acute respiratory syndrome. *Nat. Med.* 10:S88-S97.
9. Qin, E., Q. Zhu, M. Yu, B. Fan, G. Chang, B. Si, B. Yang, W. Peng, T. Jiang, B. Liu, Y. Deng, H. Liu, Y. Zhang, C. Wang, Y. Li, Y. Gan, X. Li, F. Lu, G. Tan, W. Cao, R. Yang, J. Wang, W. Li, Z. Xu, Y. Li, Q. Wu, W. Lin, Y. Han, G. Li, W. Li, H. Lu, J. Shi, Z. Tong, F. Zhang, S. Li, B. Liu, S. Liu, W. Dong, J. Wang, G. K. S. Wong, J. Yu, and H. Yang. 2003. A complete sequence and comparative analysis of a SARS-associated virus (isolate BJ01). *Chin. Sci. Bull.* 48:941-948.
10. Holmes, K. V. and L. Enjuanes. 2003. Virology: The SARS coronavirus: a postgenomic era. *Science* 300:1377-1378.
11. Holmes, K. V. 2003. SARS coronavirus: a new challenge for prevention and therapy. *J. Clin. Invest* 111:1605-1609.
12. Frana, M. F., J. N. Behnke, L. S. Sturman, and K. V. Holmes. 1985. Proteolytic cleavage of the E2 glycoprotein of murine coronavirus: host-dependent differences in proteolytic cleavage and cell fusion. *J. Virol.* 56:912-920.
13. Luytjes, W., L. S. Sturman, P. J. Bredenbeek, J. Charite, B. A. van der Zeijst, M. C. Horzinek, and W. J. Spaan. 1987. Primary structure of the glycoprotein E2 of coronavirus MHV-A59 and identification of the trypsin cleavage site. *Virology* 161:479-487.
14. Spiga, O., A. Bernini, A. Ciutti, S. Chiellini, N. Menciassi, F. Finetti, V. Causarono, F. Anselmi, F. Prischi, and N. Niccolai. 2003. Molecular modelling of S1 and S2 subunits of SARS coronavirus spike glycoprotein. *Biochem. Biophys. Res. Commun.* 310:84.
15. Bosch, B. J., B. E. Martina, Z. R. Van Der, J. Lepault, B. J. Haijema, C. Versluis, A. J. Heck, R. De Groot, A. D. Osterhaus, and P. J. Rottier. 2004. Severe acute respiratory syndrome coronavirus (SARS-CoV) infection inhibition using spike protein heptad repeat-derived peptides. *Proc. Natl. Acad. Sci. USA* 101:8455-8460.
16. Ingallinella, P., E. Bianchi, M. Finotto, G. Cantoni, D. M. Eckert, V. M. Supekar, C. Bruckmann, A. Carfi, and A. Pessi. 2004. Structural characterization of the fusion-active complex of severe acute respiratory syndrome (SARS) coronavirus. *Proc. Natl. Acad. Sci. USA* 101:8709-8714.
17. Liu, S., G. Xiao, Y. Chen, Y. He, J. Niu, C. Escalante, H. Xiong, J. Farmar, A. K. Debnath, P. Tien, and S. Jiang. 2004. Interaction between the heptad repeat 1 and 2 regions in spike protein of SARS-associated coronavirus: implication for virus fusogenic mechanism and identification of fusion inhibitors. *Lancet* 363:938-947.
18. Tripet, B., M. W. Howard, M. Jobling, R. K. Holmes, K. V. Holmes, and R. S. Hodges. 2004. Structural characterization of the SARS-coronavirus spike S fusion protein core. *J. Biol. Chem.* 279:20836-20849.

19. Chan, D. C., D. Fass, J. M. Berger, and P. S. Kim. 1997. Core structure of gp41 from the HIV envelope glycoprotein. *Cell* 89:263-273.
20. Bosch, B. J., Z. R. van der, C. A. de Haan, and P. J. Rottier. 2003. The coronavirus spike protein is a class I virus fusion protein: structural and functional characterization of the fusion core complex. *J. Virol.* 77:8801-8811.
21. Xu, Y., Z. Lou, Y. Liu, H. Pang, P. Tien, G. F. Gao, and Z. Rao. 2004. Crystal structure of SARS-CoV spike protein fusion core. *J. Biol. Chem.* 279:49414-49419.
22. Li, W. H., M. J. Moore, N. Y. Vasilieva, J. H. Sui, S. K. Wong, A. M. Berne, M. Somasundaran, J. L. Sullivan, K. Luzuriaga, T. C. Greenough, H. Y. Choe, and M. Farzan. 2003. Angiotensin-converting enzyme 2 is a functional receptor for the SARS coronavirus. *Nature* 426:450-454.
23. Dimitrov, D. S. 2003. The secret life of ACE2 as a receptor for the SARS Virus. *Cell* 115:652-653.
24. Prabakaran, P., X. Xiao, and D. S. Dimitrov. 2004. A model of the ACE2 structure and function as a SARS-CoV receptor. *Biochem. Biophys. Res. Commun.* 314:235-241.
25. Wang, P., J. Chen, A. Zheng, Y. Nie, X. Shi, W. Wang, G. Wang, M. Luo, H. Liu, L. Tan, X. Song, Z. Wang, X. Yin, X. Qu, X. Wang, T. Qing, M. Ding, and H. Deng. 2004. Expression cloning of functional receptor used by SARS coronavirus. *Biochem. Biophys. Res. Commun.* 315:439-444.
26. Xiao, X., S. Chakraborti, A. S. Dimitrov, K. Gramatikoff, and D. S. Dimitrov. 2003. The SARS-CoV S glycoprotein: expression and functional characterization. *Biochem. Biophys. Res. Commun.* 312:1159-1164.
27. Wong, S. K., W. Li, M. J. Moore, H. Choe, and M. Farzan. 2004. A 193-amino-acid fragment of the SARS coronavirus S protein efficiently binds angiotensin-converting enzyme 2. *J. Biol. Chem.* 279:3197-3201.
28. Babcock, G. J., D. J. Esshaki, W. D. Thomas, Jr., and D. M. Ambrosino. 2004. Amino acids 270 to 510 of the severe acute respiratory syndrome coronavirus spike protein are required for interaction with receptor. *J. Virol.* 78:4552-4560.
29. Cavanagh, D. 1995. The coronavirus surface glycoprotein. In The Coronaviridae. S. G. Siddell, editor. Plenum Press, New York and London. 73-114.
30. Saif, L. J. 1993. Coronavirus immunogens. *Vet. Microbiol.* 37:285-297.
31. Buchholz, U. J., A. Bukreyev, L. Yang, E. W. Lamirande, B. R. Murphy, K. Subbarao, and P. L. Collins. 2004. Contributions of the structural proteins of severe acute respiratory syndrome coronavirus to protective immunity. *Proc. Natl. Acad. Sci. USA* 101:9804-9809.
32. Yang, Z. Y., W. P. Kong, Y. Huang, A. Roberts, B. R. Murphy, K. Subbarao, and G. J. Nabel. 2004. A DNA vaccine induces SARS coronavirus neutralization and protective immunity in mice. *Nature* 428:561-564.
33. Bisht, H., A. Roberts, L. Vogel, A. Bukreyev, P. L. Collins, B. R. Murphy, K. Subbarao, and B. Moss. 2004. Severe acute respiratory syndrome coronavirus spike protein expressed by attenuated vaccinia virus protectively immunizes mice. *Proc. Natl. Acad. Sci. USA* 101:6641-6646.
34. Bukreyev, A., E. W. Lamirande, U. J. Buchholz, L. N. Vogel, W. R. Elkins, M. St Claire, B. R. Murphy, K. Subbarao, and P. L. Collins. 2004. Mucosal immunisation of African green monkeys (Cercopithecus aethiops) with an attenuated parainfluenza virus expressing the SARS coronavirus spike protein for the prevention of SARS. *Lancet* 363:2122-2127.
35. He, Y., Y. Zhou, S. Liu, Z. Kou, W. Li, M. Farzan, and S. Jiang. 2004. Receptor-binding domain of SARS-CoV spike protein induces highly potent neutralizing antibodies: implication for developing subunit vaccine. *Biochem. Biophys. Res. Commun.* 324:773-781.
36. He, Y., Y. Zhou, P. Siddiqui, and S. Jiang. 2004. Inactivated SARS-CoV vaccine elicits high titers of spike protein-specific antibodies that block receptor binding and virus entry. *Biochem. Biophys. Res. Commun.* 325:445-452.
37. Morrison, S. L., M. J. Johnson, L. A. Herzenberg, and V. T. Oi. 1984. Chimeric human antibody molecules: mouse antigen-binding domains with human constant region domains. *Proc. Natl. Acad. Sci. USA* 81:6851-6855.
38. Boulianne, G. L., N. Hozumi, and M. J. Shulman. 1984. Production of functional chimaeric mouse/human antibody. *Nature* 312:643-646.
39. Nisihara, T., Y. Ushio, H. Higuchi, N. Kayagaki, N. Yamaguchi, K. Soejima, S. Matsuo, H. Maeda, Y. Eda, K. Okumura, and H. Yagita. 2001. Humanization and epitope mapping of neutralizing anti-human Fas ligand monoclonal antibodies: structural insights into Fas/Fas ligand interaction. *J. Immunol.* 167:3266-3275.
40. Winter, G. and C. Milstein. 1991. Man-made antibodies. *Nature* 349:293-299.
41. Foote, J. and G. Winter. 1992. Antibody framework residues affecting the conformation of the hypervariable loops. *J. Mol. Biol.* 224:487-499.
42. Zhang, H., G. Wang, J. Li, Y. Nie, X. Shi, G. Lian, W. Wang, X. Yin, Y. Zhao, X. Qu, M. Ding, and H. Deng. 2004. Identification of an antigenic determinant on the S2 domain of the severe acute respiratory syndrome coronavirus spike glycoprotein capable of inducing neutralizing antibodies. *J Virol* 78:6938-6945.
43. Nie, Y., G. Wang, X. Shi, H. Zhang, Y. Qiu, Z. He, W. Wang, G. Lian, X. Yin, L. Du, L. Ren, J. Wang, X. He, T. Li, H. Deng, and M. Ding. 2004. Neutralizing antibodies in patients with severe acute respiratory syndrome-associated coronavirus infection. *J Infect. Dis.* 190:1119-1126.
44. Hofmann, H., K. Hattermann, A. Marzi, T. Gramberg, M. Geier, M. Krumbiegel, S. Kuate, K. Uberla, M. Niedrig, and S. Pohlmann. 2004. S protein of severe acute respiratory syndrome-associated coronavirus mediates entry into hepatoma cell lines and is targeted by neutralizing antibodies in infected patients. *J Virol* 78:6134-6142.
45. Lu, L., I. Manopo, B. P. Leung, H. H. Chng, A. E. Ling, L. L. Chee, E. E. Ooi, S. W. Chan, and J. Kwang. 2004. Immunological characterization of the spike protein of the severe acute respiratory syndrome coronavirus. *J Clin. Microbiol.* 42:1570-1576.
46. He, Y., Y. Zhou, H. Wu, B. Luo, J. Chen, W. Li, and S. Jiang. 2004. Identification of immunodominant sites on the spike protein of severe acute respiratory syndrome (SARS) coronavirus: implication for developing SARS diagnostics and vaccines. *J. Immunol.* 173:4050-4057.
47. Wilson, J. A., M. Hevey, R. Bakken, S. Guest, M. Bray, A. L. Schmaljohn, and M. K. Hart. 2000. Epitopes involved in antibody-mediated protection from Ebola virus. *Science* 287:1664-1666.
48. Zwick, M. B., L. L. Bonnycastle, A. Menendez, M. B. Irving, C. F. Barbas, III, P. W. Parren, D. R. Burton, and J. K. Scott. 2001. Identification and characterization of a peptide that specifically binds the human, broadly neutralizing anti-human immunodeficiency virus type 1 antibody b12. *J Virol* 75:6692-6699.
49. Sui, J., W. Li, A. Murakami, A. Tamin, L. J. Matthews, S. K. Wong, M. J. Moore, A. S. Tallarico, M. Olurinde, H. Choe, L. J. Anderson, W. J. Bellini, M. Farzan, and W. A. Marasco. 2004. Potent neutralization of severe acute respiratory syndrome (SARS) coronavirus by a human mAb to S1 protein that blocks receptor association. *Proc. Natl. Acad. Sci. USA* 101:2536-2541.
50. Subbarao, K., J. McAuliffe, L. Vogel, G. Fahle, S. Fischer, K. Tatti, M. Packard, W. J. Shieh, S. Zaki, and B. Murphy. 2004. Prior infection and passive transfer of neutralizing antibody prevent replication of severe acute respiratory syndrome coronavirus in the respiratory tract of mice. *J Virol* 78:3572-3577.
51. ter Meulen, J., A. B. H. Bakker, E. N. van den Brink, G. J. Weverling, B. E. E. Martina, B. L. Haagmans, T. Kuiken, J. de Kruif, W. Preiser, W. Spaan, H. R. Gelderblom, J. Goudsmit, and A. D. M. E. Osterhaus. 2004. Human monoclonal antibody as prophylaxis for SARS coronavirus infection in ferrets. *Lancet* 363:2139-2141.
52. Traggiai, E., S. Becker, K. Subbarao, L. Kolesnikova, Y. Uematsu, M. R. Gismondo, B. R. Murphy, R. Rappuoli, and A. Lanzavecchia. 2004. An efficient method to make human monoclonal antibodies from memory B cells: potent neutralization of SARS coronavirus. *Nat Med.* 10:871-875.
53. Welt, S., C. R. Divgi, F. X. Real, S. D. Yeh, P. Garin-Chesa, C. L. Finstad, J. Sakamoto, A. Cohen, E. R. Sigurdson, N. Kemeny, and. 1990. Quantitative analysis of antibody localization in human metastatic colon cancer: a phase I study of monoclonal antibody A33. *J. Clin Oncol.* 8:1894-1906.
54. Welt, S. and G. Ritter. 1999. Antibodies in the therapy of colon cancer. *Semin. Oncol.* 26:683-690.
55. Breedveld, F. C. 2000. Therapeutic monoclonal antibodies. *Lancet* 355:735-740.
56. Xu, Z. K., L. X. Wei, L. Y. Wang, H. T. Wang, and S. Jiang. 2002. The In vitro and in vivo protective activity of monoclonal antibodies directed against Hantaan virus: potential application for immunotherapy and passive immunization. *Biochem. Biophys. Res. Commun.* 298:552-558.

What is claimed is:

1. An isolated neutralizing monoclonal antibody capable of binding to the receptor-binding domain of the spike protein of the severe acute respiratory syndrome-associated coronavirus (SARS-CoV) wherein the antibody is produced by Hybridoma 30F9 with ATCC Accession No. PTA-6523.

* * * * *

UNITED STATES PATENT AND TRADEMARK OFFICE
CERTIFICATE OF CORRECTION

PATENT NO. : 7,629,443 B2
APPLICATION NO. : 11/351108
DATED : December 8, 2009
INVENTOR(S) : Jiang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 921 days.

Signed and Sealed this

Second Day of November, 2010

David J. Kappos
*Director of the United States Patent and Trademark Office*